United States Patent
Hossick-Schott et al.

(10) Patent No.: US 7,459,369 B2
(45) Date of Patent: Dec. 2, 2008

(54) HIGH CAPACITANCE LOW RESISTANCE ELECTRODE

(75) Inventors: Joachim Hossick-Schott, Minneapolis, MN (US); Ann M. Crespi, Mobile, AL (US)

(73) Assignee: Medtronic, Inc., Minneapolis, MN (US)

( * ) Notice: Subject to any disclaimer, the term of this patent is extended or adjusted under 35 U.S.C. 154(b) by 126 days.

(21) Appl. No.: 11/278,282

(22) Filed: Mar. 31, 2006

(65) Prior Publication Data

US 2007/0232037 A1    Oct. 4, 2007

(51) Int. Cl.
*H01L 21/20* (2006.01)
(52) U.S. Cl. .................. 438/381; 438/171; 438/210; 438/239; 257/E21.008; 257/E21.011
(58) Field of Classification Search .......... 438/171, 438/329; 257/E21.351, E21.045, E21.061, 257/E21.466, E21.477
See application file for complete search history.

(56) References Cited

U.S. PATENT DOCUMENTS

| | | | |
|---|---|---|---|
| 3,243,316 A | | 3/1966 | O'Nan et al. |
| 5,369,547 A | | 11/1994 | Evans |
| 6,807,048 B1 | | 10/2004 | Nielsen et al. |
| 2004/0064155 A1 | * | 4/2004 | Norton et al. .................. 607/2 |
| 2004/0240144 A1 | * | 12/2004 | Schott et al. ................. 361/302 |
| 2005/0090108 A1 | | 4/2005 | Hossick-Schott |
| 2005/0098242 A1 | | 5/2005 | Hossick-Schott |
| 2005/0146841 A1 | | 7/2005 | Schott et al. |
| 2005/0177193 A1 | | 8/2005 | Nielsen et al. |

* cited by examiner

*Primary Examiner*—Walter L Lindsay, Jr.
*Assistant Examiner*—Cheung Lee
(74) *Attorney, Agent, or Firm*—Carol F. Barry

(57) ABSTRACT

Methods are provided for manufacturing an electrode. In one exemplary embodiment, the method includes the steps of contacting the silver layer with vanadium oxide, and heating the silver layer and vanadium oxide in an oxygen-containing atmosphere to form a silver vanadium oxide layer chemically bonded to the metal substrate.

17 Claims, 3 Drawing Sheets

HIGH CAPACITANCE LOW RESISTANCE ELECTRODE

FIELD OF THE INVENTION

The present invention generally relates to implantable medical devices, and more particularly to cathode electrodes of high-voltage capacitors, such as electrolytic capacitors, that are capable of high capacitance and low resistance and are for use in implantable medical devices.

BACKGROUND OF THE INVENTION

Implantable medical devices (IMDs) are well known for providing a variety of therapies to humans. For example, implantable cardiac defibrillators are used to monitor the electrical activity of the heart of a patient, detect ventricular fibrillation, and in response to that detection, deliver appropriate therapy pulses to restore a normal heart rhythm. Implantable neurostimulators have been used to stimulate the spinal cord and brain for a variety of treatments, including the treatment of chronic pain and the treatment of peripheral vascular disease. Implantable pacemakers generate and apply electric stimuli in the form of pulses to the tissue of a heart to control the timing of the contractions of the heart.

The above-described IMDs, and other similar devices, utilize an internal power source, or electrochemical cell, to provide the power required for a desired application. Implantable cardiac defibrillators also use an electrolytic capacitor which is charged by the internal power source and subsequently discharged in order to provide electrical pulse therapy. The electrolytic capacitor includes an anode, a cathode, and electrolyte disposed therebetween. Typically, the anode is constructed from metal, such as aluminum, tantalum, titanium, or other suitable metals capable of forming anodic oxides upon anodization. The cathode may be configured as a coating on a metal, for example, graphite on titanium as disclosed in U.S. Pat. No. 7,002,790, and may be applied to the metal by, for example, chemical vapor deposition, physical vapor deposition, or spraying.

Alternatively, the cathode may be configured as a sheet metal which has been treated, for example by etching, in order to obtain a larger surface area.

In instances in which a high capacitance, low resistance capacitor is preferred, silver vanadium oxide may be used to coat the cathode. It has been found that silver vanadium oxide alone yields relatively high capacitance and that the capacitance of compressed pellets consisting of silver vanadium oxide powder can be significant. However, the electrical conductivity of silver vanadium oxide pellets is comparatively low, resulting in an unacceptably high equivalent serial resistance ("ESR") of the finished capacitor. In addition, forming a durable coating of silver vanadium oxide powder on a metallic substrate without diminishing the capacitance is relatively difficult.

Accordingly, there is a need for a method of producing a silver vanadium oxide coating on a cathode that yields high capacitances and low ESR values in order to render the electrode suitable for use in a high-voltage defibrillator capacitor, where capacitance values of greater than approximately 10 mF/cm$^2$ are typically preferred. Additionally, it would be desirable for the method to be relatively simple and cost-effective to use. Furthermore, other desirable features and characteristics of the present invention will become apparent from the subsequent detailed description of the invention and the appended claims, taken in conjunction with the accompanying drawings and this background of the invention.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

Methods are provided for manufacturing an electrode. In one exemplary embodiment, the electrode is manufactured from a metal substrate including a silver layer thereon and the method includes the steps of contacting the silver layer with vanadium oxide, and heating the silver layer and vanadium oxide in an oxygen-containing atmosphere to form a silver vanadium oxide layer chemically bonded to the metal substrate.

In another exemplary embodiment, the method includes the steps of forming a silver coating on a metal substrate, oxidizing the silver coating on the metal substrate, contacting the oxidized silver coating with vanadium oxide, and heating the oxidized silver coating and vanadium oxide in an oxygen-containing atmosphere to thereby cause a chemical reaction therebetween to form a silver vanadium oxide layer.

In still another exemplary embodiment, the method includes the steps of oxidizing silver on a metal substrate, contacting the oxidized silver with vanadium oxide, heating the oxidized silver and vanadium oxide to thereby cause a chemical reaction therebetween to form a silver vanadium oxide layer, and diffusing at least a portion of the silver vanadium oxide layer into the metal substrate to thereby chemically bond the silver vanadium oxide layer to thereto.

The following detailed description of the invention is merely exemplary in nature and is not intended to limit the scope, applicability, or configuration of the invention in any way. Rather, the following description provides a convenient illustration for implementing exemplary embodiments of the invention. Various changes to the described embodiments may be made in the function and arrangement of the elements described herein without departing from the scope of the invention.

Figure 1:
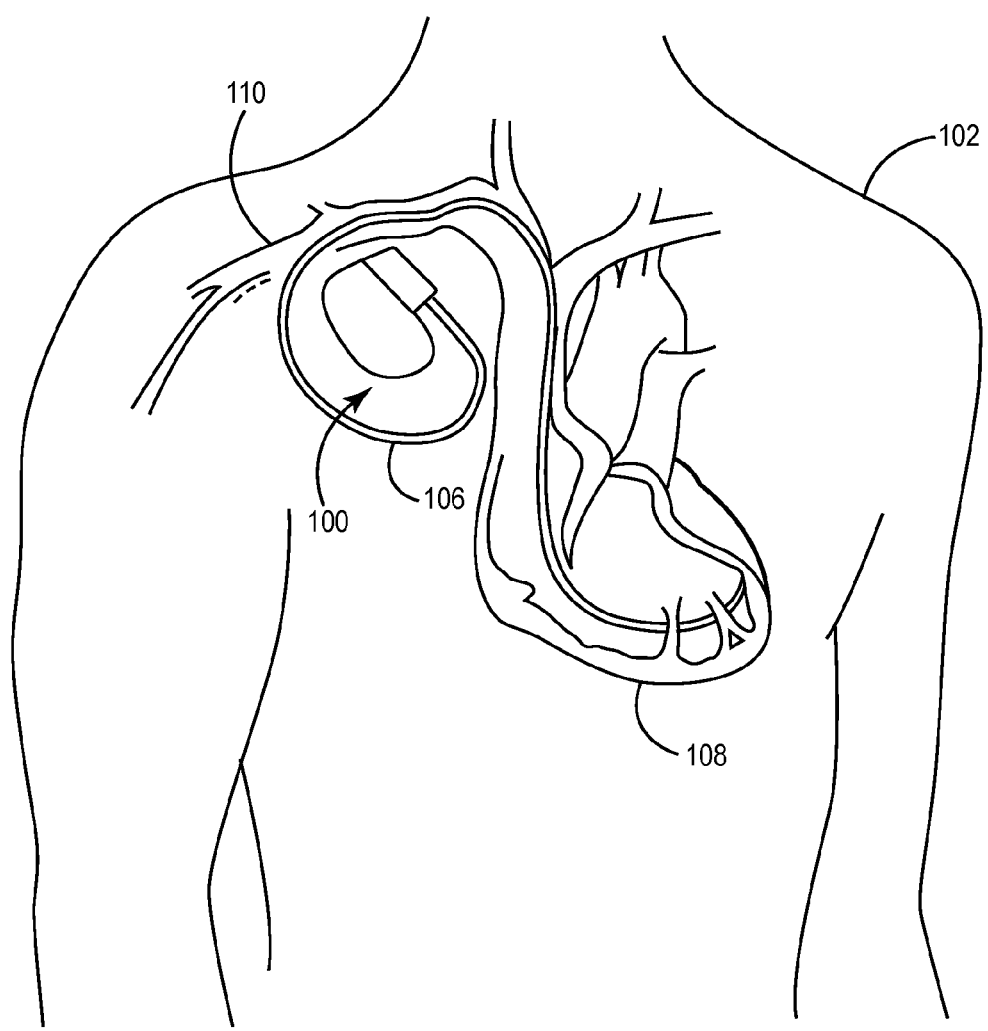
FIG. 1 is a diagram showing a typical placement of an IMD in a patient.

FIG. 1 is an illustration showing generally where an implantable cardiac device (IMD) 100 may be placed in a patient 102. IMD 100 is illustrated herein as a defibrillator. One or more leads 106 are electrically coupled to IMD 100 in a conventional manner and extend into the patient's heart 108 via a vein 110. Disposed generally near the distal end of lead 106 are one or more exposed conductive electrodes for sensing electrical cardiac signals and/or for delivering electrical stimuli or other therapies to heart 108. Lead 106 may be implanted with its distal end in either the atrium or the ventricle of heart 108. Lead 106 is preferably a bipolar lead such that lead 106 actually has two separate and mutually insulated leads, the first having a terminal at the distal end of lead 106 and the second having a terminal near, but set back from the distal end. Such leads are well known in the art.

Figure 2:
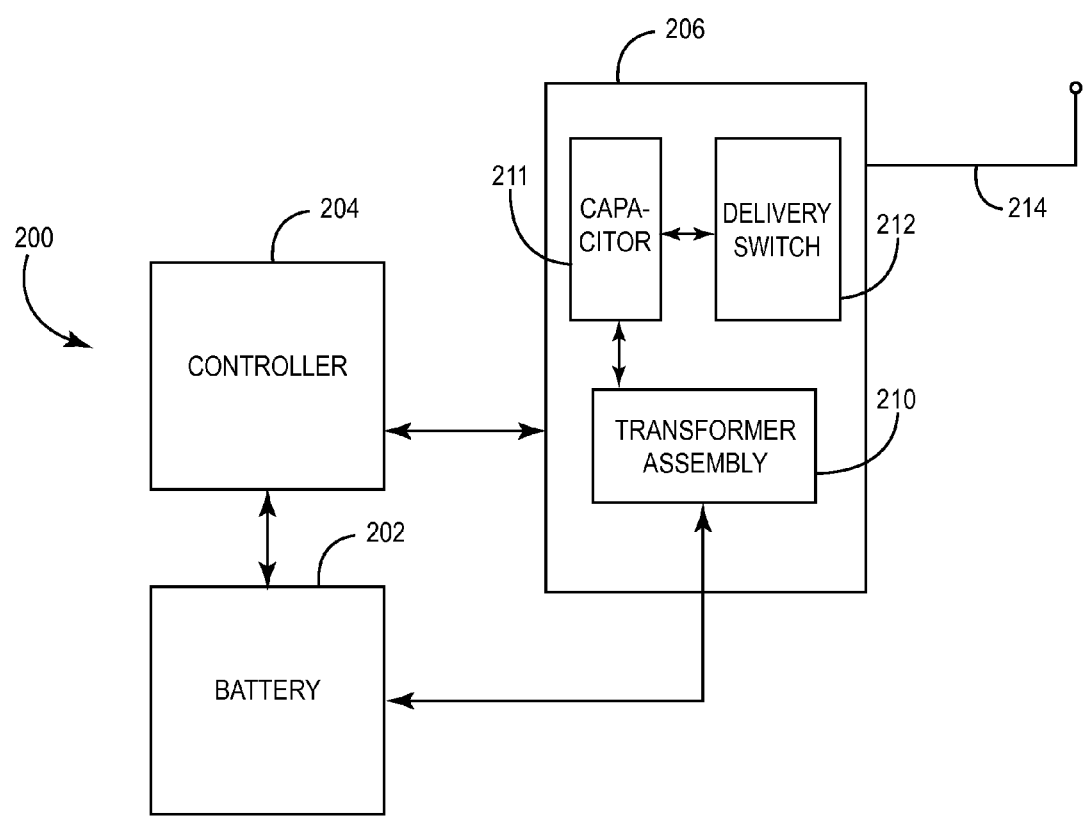
FIG. 2 is a simplified block diagram of a portion of circuitry that may be implemented within the IMD of FIG. 1.

FIG. 2 is a simplified block diagram of exemplary circuitry 200 that may be housed within IMD 100. Circuitry 200 is configured to produce pulses that are used to pace the heart;

i.e., cause a depolarization of the heart tissue or issue a defibrillation pulse to shock the heart from arrhythmia to a normal heart beat.

Circuitry 200 includes a battery 202 electrically coupled to a controller 204 and a pulse generating circuit 206. Although circuitry 200 includes three components, it will be appreciated that fewer or more components may be employed. Battery 202 is configured to provide operating power to controller 204 and pulse generating circuit 206 and is preferably capable of operating at low current drains over a long duration and high current pulses when therapy to patient 102 is required. Any one of numerous types of appropriate batteries may be used, such as, for example lithium/silver vanadium oxide batteries.

Figure 3:
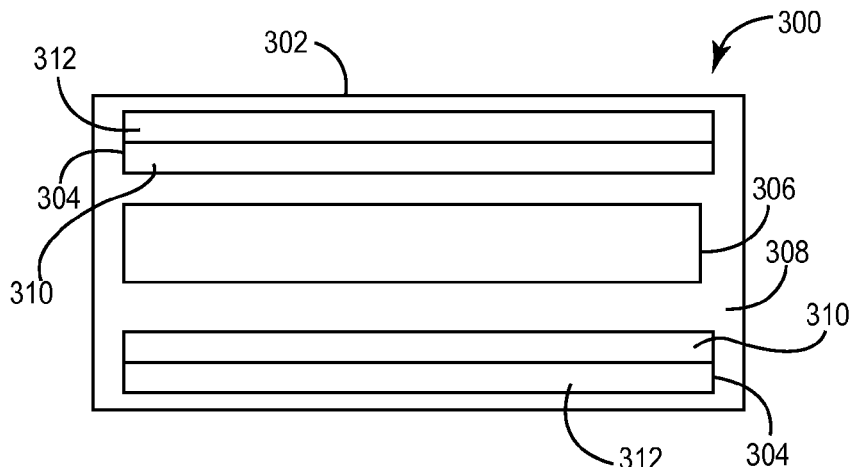
FIG. 3 is a cross-sectional view of an exemplary capacitor that may be included in the circuitry of FIG. 2.

Pulse generating circuit 206 is configured to generate low or high energy pulses and to deliver the pulses to patient 102 in response to control signals from controller 204. In this regard, pulse generating circuit 206 includes a transformer assembly 210 that is coupled to at least one capacitor 211, which is in turn coupled to a delivery switch 212. Transformer assembly 210 converts the battery voltage to an appropriate voltage suitable for charging the capacitor. Electronic charge is accumulated in capacitor 211 until the therapy pulse is ready to be delivered, at which point delivery switch 212 is switched from an off position to an on position thereby routing the therapy pulse to appropriate leads 214. [18] FIG. 3 is a cross-sectional view of an exemplary capacitor 300 that may be used in pulse generating circuit 206. Although a single capacitor 300 is shown, more may alternatively be employed, in which case the capacitors would be preferably electrically coupled in series; however, any other suitable configuration may alternatively be employed. Moreover, the capacitors may all be equally sized and configured, or may have a different sizes and configurations.

Capacitor 300 may have any one of a number of configurations suitable for storing a desired charge. For example, capacitor 300 can include a casing 302 having any one of several shapes (e.g. clam shell, D-shaped, or etc.) within which components of capacitor 300 may be disposed. No matter the particular configuration, however, capacitor 300 includes a cathode 304, an anode 306, a suitable separator between cathode 304 and anode 306 (for example, spacing therebetween), and an electrolyte 308, as shown in FIG. 3. Generally, cathode 304 and anode 306 are disposed in series and are each made of conductive materials. Cathode 304 and anode 306 are preferably spaced apart from each other, and electrolyte 308 is disposed therebetween. In some embodiments, an interior surface of casing 302 may serve as a cathode and anode 306, the separator, and electrolyte 308 may be disposed therein. Electrolyte 308 may comprise any one of numerous conventional electrolytic solutions. For example, electrolyte 308 may comprise ammonium salts (e.g., ammonium acetate) dissolved in water and glycol, or phosphoric acid, or any other compositions such as those specified in U.S. Pat. Nos. 6,939,774, 6,859,354, and 6,788523. The selection of the particular electrolyte used in capacitor 300 may depend upon factors such as achieving a desired conductivity of the electrolyte.

Cathode 304 is configured to balance the charge of anode 306, and not to contribute significantly to the equivalent serial resistance (ESR) of capacitor 300.

In this regard, cathode 304 preferably includes a silver vanadium oxide layer 310 chemically bonded or chemisorbed to a metallic substrate or base material 312.

Substrate 312 is constructed from a metal that is preferably durable, weldable, and resistant to chemical erosion. Suitable metals include, but are not limited to titanium, tantalum, niobium, aluminum, zirconium, silver, stainless steel, and alloys of any one or more of the foregoing metals. In one example, substrate 312 is made of a silver-coated titanium sheet. Silver vanadium oxide layer 310 is chemically bonded to and disposed over at least a portion of substrate 312 to provide cathode 304 with a specific capacitance on the order of about 10 $mF/cm^2$ or greater when capacitor 300 is in operation.

Figure 4:
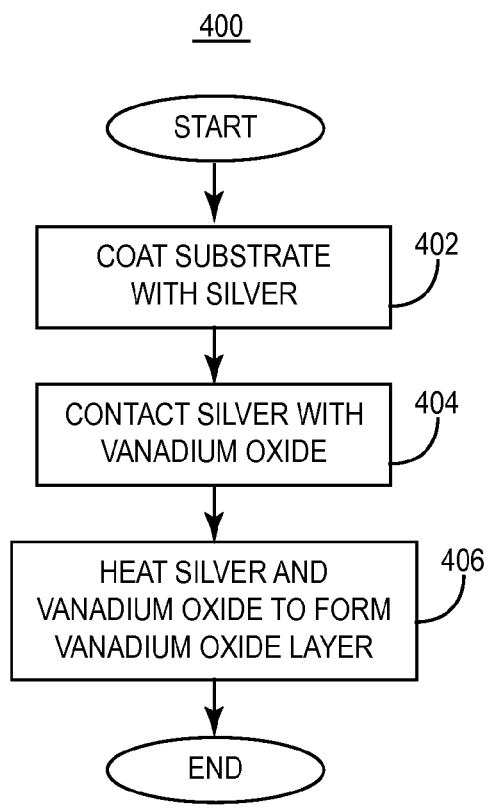
FIG. 4 is a flow diagram of an exemplary method of manufacturing the capacitor illustrated in FIG. 3.

FIG. 4 is a flow diagram illustrating an exemplary method 400 for chemically bonding a silver vanadium oxide layer to a substrate. Generally, the substrate is first coated with silver, as shown at 402. Next, the silver coating is contacted directly with vanadium oxide (step 404). The oxidized or unoxidized silver coating and vanadium oxide are then heated in an oxygen-containing atmosphere to thereby cause a chemical reaction therebetween to form the silver vanadium oxide layer and to chemically bond the silver vanadium oxide layer to the substrate, as shown at 406.

As briefly mentioned above, the substrate is first coated with silver (step 402). The silver coating is preferably formed over a side of the substrate that may be placed proximate anode 306. However, in other embodiments, substantially all of the substrate may include the silver coating. Silver may be deposited or otherwise formed on the substrate using any one of a variety of conventional techniques. For example, silver may be deposited over the substrate using chemical vapor deposition, physical vapor deposition, sputtering, electroplating and the like. Alternatively, titanium-silver alloys may be used as substrates. It will be appreciated, however, that in cases in which the substrate is constructed of silver or silver-containing alloys, step 402 may be omitted.

In some embodiments, the silver coated substrate may be subjected to an oxidation step. In such case, an oxide is formed on the substrate by, for example, immersing the silver coated substrate in an electrolyte and applying a current, for example, an anodic potential of about one volt, thereto. The electrolyte may include any one of numerous conventionally used constituents for oxidizing silver. In one exemplary embodiment, the electrolyte may be a solution that includes constituents such as water, boric acid, and ammonium pentaborate. In other embodiments, the silver surface may react directly with vanadium oxide and the oxidation step may be omitted.

Next, the silver coating (oxidized or unoxidized) is contacted with vanadium oxide, as shown at 404. Contact between the silver coating and vanadium oxide may be accomplished using any one of a number of conventional techniques. For example, vanadium oxide may be reactively sputtered onto the silver coating. In another example, vanadium oxide powder is mixed with an alcohol having a carbon chain of three or more, e.g., glycerol, to form a suspension that is deposited onto the silver coating via spray-coating or a printing method, e.g., ink jet printing, as disclosed in U.S. Patent Appn. Pub. No. 2005/0089711. Alternatively, the substrate may be immersed into a container within which the suspension is disposed.

Next, the silver coating and vanadium oxide are heat treated at a predetermined temperature for a predetermined duration of time to form the silver vanadium oxide layer (step 406). This step is preferably performed in an oxygen-containing atmosphere. The heat treatment causes the alcohol of the suspension to vaporize and causes the silver vanadium oxide layer to diffuse into and chemically bond to the substrate. In one exemplary embodiment, the silver coating and vanadium oxide is heated to a temperature between about 400° C. and about 600° C. for about 2 hours. However, any other suitable environment may alternatively be employed.

Thus, a method has been provided that produces a chemisorbed silver vanadium oxide coating on a cathode substrate that yields capacitance values on the order of approximately 10 mF/cm$^2$ or greater. Additionally, the method is relatively simple and cost-effective to use.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A method for manufacturing an electrode from a metal substrate including a silver layer thereon, the method comprising the steps of:
    oxidizing the silver layer on the metal substrate by subjecting the silver layer to an anodic potential of about one volt;
    contacting the silver layer with vanadium oxide; and
    heating the silver layer and vanadium oxide in an oxygen-containing atmosphere to form a silver vanadium oxide layer chemically bonded to the metal substrate.

2. The method of claim 1, wherein the metal substrate comprises titanium and the method further comprises coating the titanium metal substrate with silver to form the silver layer.

3. The method of claim 1, wherein the step of oxidizing further comprises exposing the silver layer to an electrolyte comprising water, boric acid and ammonium pentaborate.

4. The method of claim 1, wherein the step of contacting comprises contacting the silver layer with a vanadium oxide powder suspended in an alcohol.

5. The method of claim 1, wherein the step of contacting comprises reactive sputtering vanadium onto the silver layer in the oxygen-containing atmosphere.

6. The method of claim 1, wherein the step of heating comprises heating the substrate, the silver layer, and vanadium oxide to between about 400° C. and about 600° C. in the oxygen-containing atmosphere.

7. The method of claim 1, wherein the step of heating comprises diffusing the vanadium oxide into the silver layer to form the silver vanadium oxide layer.

8. A method for manufacturing an electrode comprising the steps of:
    forming a silver coating on a metal substrate;
    electrochemically oxidizing the silver coating on the metal substrate by exposing the silver coating to anodic potentials on the order of one volt in a suitable electrolyte;
    contacting the oxidized silver coating with vanadium oxide; and
    heating the oxidized silver coating and vanadium oxide in an oxygen-containing atmosphere to thereby cause a chemical reaction therebetween to form a silver vanadium oxide layer.

9. The method of claim 8, wherein the electrolyte comprises water, boric acid, and ammonium pentaborate.

10. The method of claim 8, wherein the metal substrate comprises titanium and the method further comprises coating the titanium metal substrate with silver.

11. The method of claim 8, wherein the step of contacting comprises contacting the oxidized silver coating with a vanadium oxide powder suspended in an alcohol.

12. The method of claim 8, wherein the step of contacting comprises reactive sputtering the vanadium oxide onto the oxidized silver coating.

13. The method of claim 8, wherein the step of heating comprises heating the oxidized silver coating and vanadium oxide to between about 400° C. and about 600° C.

14. A method for manufacturing a cathode comprising the steps of:
    oxidizing silver on a metal substrate;
    contacting the oxidized silver with vanadium oxide;
    heating the oxidized silver and vanadium oxide to thereby cause a chemical reaction therebetween to form a silver vanadium oxide layer; and
    diffusing at least a portion of the silver vanadium oxide layer into the metal substrate to thereby chemically bond the silver vanadium oxide layer to thereto.

15. The method of claim 14, wherein the step of contacting comprises contacting the oxidized silver with a vanadium oxide powder suspended in alcohol.

16. The method of claim 14, wherein the step of contacting comprises reactive sputtering the vanadium oxide onto the oxidized silver.

17. The method of claim 14, wherein the step of heating comprises heating the oxidized silver and vanadium oxide to between about 400° C. and about 600° C.

* * * * *

UNITED STATES PATENT AND TRADEMARK OFFICE
CERTIFICATE OF CORRECTION

PATENT NO. : 7,459,369 B2 Page 1 of 1
APPLICATION NO. : 11/278282
DATED : December 2, 2008
INVENTOR(S) : Hossick-Schott et al.

It is certified that error appears in the above-identified patent and that said Letters Patent is hereby corrected as shown below:

Col. 6, Line 1, Claim 7, delete "of beating comprises...." and insert in place thereof --of heating comprises...--

Signed and Sealed this

Eleventh Day of August, 2009

David J. Kappos
*Director of the United States Patent and Trademark Office*